United States Patent
Wachtel et al.

(10) Patent No.: US 8,944,054 B2
(45) Date of Patent: Feb. 3, 2015

(54) MEDICINE DISPENSATION DEVICE

(75) Inventors: Herbert Wachtel, Ingelheim (DE);
Johannes Geser, Ingelheim (DE);
Burkhard P. Metzger, Ingelheim (DE);
Michael Spallek, Ingelheim (DE);
Michael Krueger, Ingelheim (DE);
Hubert Kunze, Dortmund (DE); Achim Moser, Chemnitz (DE); Elmar Mock, Colombier (CH); Antonino Lanci, Bern (CH); Andre Klopfenstein, La Neuveville (CH)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 1290 days.

(21) Appl. No.: 12/296,980

(22) PCT Filed: Apr. 13, 2007

(86) PCT No.: PCT/CH2007/000179
§ 371 (c)(1),
(2), (4) Date: Dec. 29, 2008

(87) PCT Pub. No.: WO2007/118341
PCT Pub. Date: Oct. 25, 2007

(65) Prior Publication Data
US 2009/0173345 A1 Jul. 9, 2009

(30) Foreign Application Priority Data

Apr. 13, 2006 (EP) ..................................... 06405162

(51) Int. Cl.
*A61M 15/00* (2006.01)

(52) U.S. Cl.
CPC ....... *A61M 15/0045* (2013.01); *A61M 15/0003* (2014.02); *A61M 15/003* (2014.02); *A61M 15/0048* (2014.02); *A61M 15/0051* (2014.02); *A61M 2202/064* (2013.01)
USPC ............ 128/203.21; 128/200.24; 128/203.12; 128/203.15

(58) Field of Classification Search
USPC ............. 128/203.15, 203.21, 200.14, 200.17, 128/200.23, 203.12, 205.21; 604/58; 221/69, 75; 222/144, 167
See application file for complete search history.

(56) References Cited

U.S. PATENT DOCUMENTS 3,410,450 A * 11/1968 Fortenberry ....................... 221/7
3,870,046 A * 3/1975 Elliott ........................ 128/203.15
(Continued)

FOREIGN PATENT DOCUMENTS

| DE | 195 00 764 A1 | 7/1996 |
| EP | 1 003 478 B1 | 5/2000 |

(Continued)

*Primary Examiner* — Annette Dixon
(74) *Attorney, Agent, or Firm* — Michael P. Morris; David L. Kershner

(57) ABSTRACT

A medicine dispensation device, in particular a multi-dose powder inhalator, for the dispensing of individual doses of medicine that has a number of medicine chambers contained in a medicine magazine shaped like a continuous loop. The medicine chambers form groups in such a manner that a mouthpiece reaches the different groups by an essentially complete rotation of the medicine magazine. This enables several medicine chambers—typically one, two or three—to be situated between two successive intake positions, which allows for a high density of medicine chambers and thus creates an inhalation device, which can be handled comfortably even when containing a great number of individual doses.

11 Claims, 2 Drawing Sheets

(56) References Cited

U.S. PATENT DOCUMENTS

| | | | |
|---|---|---|---|
| 4,627,432 A | | 12/1986 | Newell et al. |
| 4,811,731 A | * | 3/1989 | Newell et al. ............ 128/203.15 |
| 5,207,217 A | * | 5/1993 | Cocozza et al. ......... 128/203.21 |
| 5,492,112 A | * | 2/1996 | Mecikalski et al. ..... 128/203.15 |
| 5,590,645 A | | 1/1997 | Davies et al. |
| 5,699,789 A | * | 12/1997 | Hendricks ............... 128/203.15 |
| 6,237,590 B1 | | 5/2001 | Leedom et al. |
| 6,679,254 B1 | | 1/2004 | Rand et al. |
| 2006/0191931 A1 | * | 8/2006 | Rand ........................... 220/23.4 |

FOREIGN PATENT DOCUMENTS

| | | | |
|---|---|---|---|
| WO | WO2004/045487 | * | 6/2004 |
| WO | 2004/091703 A1 | | 10/2004 |

* cited by examiner

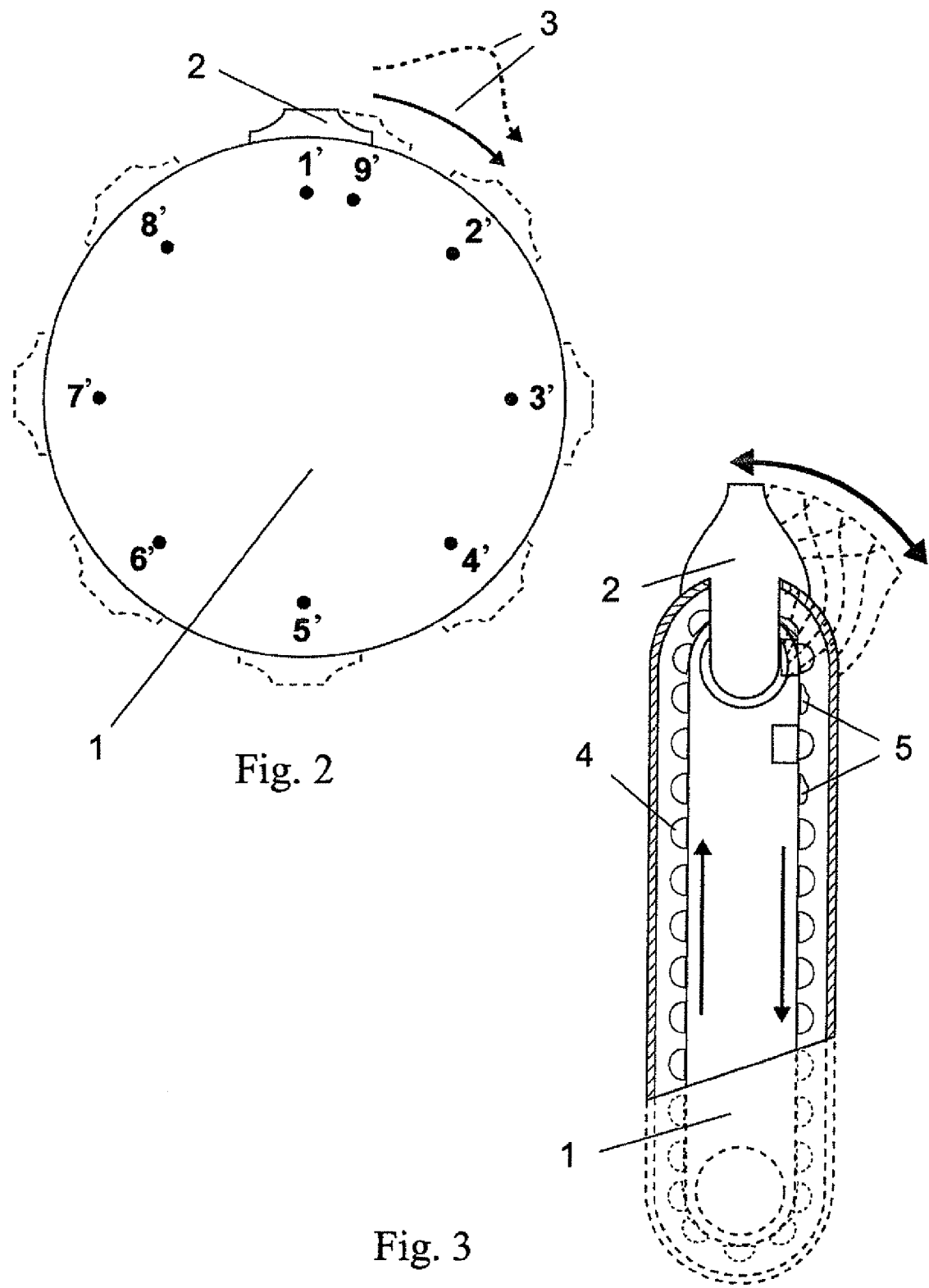

MEDICINE DISPENSATION DEVICE

CROSS REFERENCE TO RELATED APPLICATION

This application is the national phase entry under 35 U.S.C. §371 of International Application No. PCT/CH2007/000179, filed Apr. 13, 2007, which claims priority to European Application No. EP 06405162.6, filed Apr. 13, 2006, each of which is hereby incorporated by reference in its entirety.

BACKGROUND OF THE INVENTION

1. Field of the Invention

The invention lays in the field of medicine dispensation devices with a multiple magazine; in particular, in the field of inhalation devices for drugs in powdered form, and concerns a medicine dispensation device according to the generic term of the independent claim.

2. Description of Related Art

An inhalation device transporting a blister pack of circularly arranged blisters by rotation is known from the U.S. Pat. No. 4,627,432. The blisters set in the blister pack are successively brought into an inhalation position and pierced by a lever in order to be opened. The certain elevation necessary for the piercing renders the installation relatively large. If, as, e.g., described in the document U.S. Pat. No. 5,590,645, an opening mechanism is to be installed near or in a mouthpiece considerable force is required for the change of position and opening. In order to ease the use of the device this power is preferably distributed across some distance. However, to transfer this distance, or an increased effort of movement respectively, to a sideway motion of the mouthpiece would require that the individual blisters in the blister pack would have to be interspaced accordingly. This is rather disadvantageous in the case of multiple-dose inhalers containing as many individual doses as possible and would be disadvantageous for the need of small handy devices.

In several documents, e.g., in U.S. Pat. No. 6,237,590, in U.S. Pat. No. 6,679,254 or in German Patent Application DE 195 00 764, medicine dipensation devices are disclosed, which discribe a maximized number of medicine chambers in a discoidal medicine magazine. Therein the medicine chambers are arranged in two to three conventric circles, wherein firstly all of the chambers of the first circle are apprached and then the chambers of the following circle, which circle is lying more centrally. Possibly, e.g., as in German Patent Application DE 195 00 764, a circle may also be skipped. A disadvantage of this device is on one hand that an advancing or opening installation, which has to allow for a radial or central movement, is rather complex. On the other hand the individual chambers on the concentric circles may be arranged only as close as the opening installation allows. An advancing arrangement with a constant advance and at the same time a high chamber concentration is not possible with these devices.

SUMMARY OF THE INVENTION

The object of the invention is to create a drug-dispensation device which offers sufficient mobility for the positioning and opening of a medicine chamber while the medicine chambers are densely packed in a medicine magazine, in particular also suited for medicine magazines with chambers set in a circle.

The object is achieved by the medicine dispensation that, preferably, is a multiple-dose powder inhaler, for the dispensation of individual units of medicine comprises a multitude of medicine chambers in a medicine magazine, wherein the magazine with its chambers appears in the shape of a continuous loop. The medicine magazine and a mouthpiece, through which a patient can take—e.g., inhale—a drug, can be moved in relation to each other in order to align each medicine chamber successively with the mouthpiece. The medicine chambers of the endless or continuous loop form groups in such a manner that the mouthpiece reaches different groups by an essentially complete rotation of the medicine magazine, i.e. after an essentially complete turn of the loop.

An essentially complete turn means that a mouthpiece, which sets out in a medicine-chamber position x, after an essentially complete turn is situated preferably in a medicine-chamber position x+1 or x−1. As both, a mouthpiece and a medicine magazine or a casing can be shifted in relation to each other, the rotation can relate to the mouthpiece moving around the magazine or the casing, or to a medicine magazine rotating essential by 360°, or slightly more than 360°, in relation to a mouthpiece or the casing.

The medicine dispensation device according to the invention makes it possible that two successive intake positions do not correspond with two adjacent chamber positions. Between two successive intake positions there may be several medicine chambers, typically one, two or three.

Thus, the lever or advance required for the opening of a medicine chamber may be as long as necessary, without losing the space in between as storage for medicine chambers.

This allows for a very high medicine chamber density and thus the creation of an inhalator containing individual drug portions for several weeks or months, e.g., 30 to 60 individual doses, without the need to change medicine magazines. This applies to consistent inhalator sizes, possibly also to smaller ones. The skipping of individual medicine chambers during a certain rotation offers the path necessary for an elevation of an opening mechanism for a medicine chamber, e.g., by piercing. It is furthermore possible to spread the force required for the shifting of a magazine and for the opening of a chamber across a longer path without losing storage space for medicine chambers. This is particularly advantageous in the case of disc-shaped inhalators, where a medicine magazine has the shape of a ring wheel and the individual medicine chambers are placed in a circle within. If the shifting/transporting and opening motions are to be integrated in a movement e.g., of a mouthpiece along the outer circumference of the ring wheel, an extensive advance of the mouthpiece is possible while simultaneously allowing for the medicine chambers to be positioned more closely than at the corresponding advancing distance.

Thus varying opening mechanisms such as piercing, peeling or scraping can be directly integrated in, or combined with the motion of a mouthpiece.

In a preferred embodiment, mouthpiece and medicine magazine can be moved only in one direction in relation to each other, the medicine chambers are equidistantly positioned, and the advance comprises a consistent distance.

A medicine magazine suitable for the drug-dispensation device, with the medicine chambers positioned therein, is set in a continuous loop. This can be essentially any kind of cyclic arrangement of medicine chambers. Typical examples are wheel rings with medicine magazines placed in a circular fashion or endless blister loops, e.g. in a circular or oval setting. In the illustrated embodiments, a single endless loop is shown and the center points of each medicine chamber is positioned along the single continuouse loop.

The drug-dispensation device comprises preferably a display to indicate in which medicine chamber or intake position the mouthpiece is situated. It is further possible to give information about a group of medicine chambers in such a display, which is of a particular advantage in installations with magazines comprising e.g., groups of medicine chambers containing varying doses or preparations of a drug.

The preferred amount of medicine chambers or medicine single dose units for the device ranges from 1 to 100, or up to 200 individual medicine doses, preferably in the range of 1 to 60, e.g., between 7 and 180 or 14 and 150, e.g., 30-120, 45-100, 30, 90, 60, 120. In the case of inhalation devices the preferred maximum number is 60 individual doses, both, for therapeutic reasons and for the sake of convenient handling.

As pharmaceutically effective substances, substance formulations or substance compounds all inhalable combinations are employed, including e.g., inhalable macromolecules, as disclosed in EP 1 003 478. The preferred application is with substances, substance formulations or substance compounds used in inhalators for the treatment of respiratory diseases.

The compounds specified below may be used in the apparatus on their own or in combination. In the compounds specified below, W is a pharmacologically active substance and (for example) is selected from among the betamimetics, anticholinergics, corticosteroids, PDE4-inhibitors, LTD4-antagonists, EGFR-inhibitors, dopamine agonists, H1-antihistamines, PAF-antagonists and PI3-kinase inhibitors. Moreover, double or triple combinations of W may be combined and used in the apparatus accin, Combinations of W might be, for example:

W denotes a betamimetic, combined with an anticholinergic, corticosteroid, PDE4-inhibitor, EGFR-inhibitor or LTD4-antagonist, W denotes an anticholinergic, combined with a betamimetic, corticosteroid, PDE4-inhibitor, EGFR-inhibitor or LTD4-antagonist, W denotes a corticosteroid, combined with a PDE4-inhibitor, EGFR-inhibitor or LTD4-antagonist, W denotes a PDE4-inhibitor, combined with an EGFR-inhibitor or LTD4-antagonist, W denotes an EGFR-inhibitor, combined with an LTD4-antagonist.

The compounds used as betamimetics are preferably compounds selected from among albuterol, arformoterol, bambuterol, bitolterol, broxaterol, carbuterol, clenbuterol, fenoterol, formoterol, hexoprenaline, ibuterol, isoetharine, isoprenaline, levo salbutamol, mabuterol, meluadrine, metaproterenol, orciprenaline, pirbuterol, procaterol, reproterol, rimiterol, ritodrine, salmefamol, salmeterol, soterenol, sulphonterol, terbutaline, tiaramide, tolubuterol, zinterol, CHF-1035, HOKU-81, KUL-1248 and 3-(4-{6-[2-hydroxy-2-(4-hydroxy-3-hydroxymethyl-phenyl)-ethylamino]-hexyloxy}-butyl)-benzyl-sulphonamide
5-[2-(5,6-diethyl-indan-2-ylamino)-1-hydroxy-ethyl]-8-hydroxy-1H-quinoline-2-one
4-hydroxy-7-[2-{[2-{[3-(2-phenylethoxy)propyl]sulphonyl}ethyl]-amino}ethyl]-2(3H)-benzothiazolone
1-(2-fluoro-4-hydroxyphenyl)-2-[4-(1-benzimidazolyl)-2-methyl-2-butylamino]ethanol
1-[3-(4-methoxybenzyl-amino)-4-hydroxyphenyl]-2-[4-(1-benzimidazolyl)-2-methyl-2-butylamino]ethanol
1-[2H-5-hydroxy-3-oxo-4H-1,4-benzoxazin-8-yl]-2-[3-(4-N,N-dimethylaminophenyl)-2-methyl-2-propylamino]ethanol
1-[2H-5-hydroxy-3-oxo-4H-1,4-benzoxazin-8-yl]-2-[3-(4-methoxyphenyl)-2-methyl-2-propylamino]ethanol
1-[2H-5-hydroxy-3-oxo-4H-1,4-benzoxazin-8-yl]-2-[3-(4-n-butyloxyphenyl)-2-methyl-2-propylamino]ethanol
1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol
5-hydroxy-8-(1-hydroxy-2-isopropylaminobutyl)-2H-1,4-benzoxazin-3-(4H)-on
1-(4-amino-3-chloro-5-trifluoromethylphenyl)-2-tert.-butylamino)ethanol
6-hydroxy-8-{1-hydroxy-2-[2-(4-methoxy-phenyl)-1,1-dimethyl-ethylamino]-ethyl}-4H-benzo[1,4]oxazin-3-one
6-hydroxy-8-{1-hydroxy-2-[2-(ethyl 4-phenoxy-acetate)-1,1-dimethyl-ethylamino]-ethyl}-4H-benzo[1,4]oxazin-3-one
6-hydroxy-8-{1-hydroxy-2-[2-(4-phenoxy-acetic acid)-1,1-dimethyl-ethylamino]-ethyl}-4H-benzo[1,4]oxazin-3-one
8-{2-[1,1-dimethyl-2-(2,4,6-trimethylphenyl)-ethylamino]-1-hydroxy-ethyl}-6-hydroxy-4H-benzo[1,4]oxazin-3-one
6-hydroxy-8-{1-hydroxy-2-[2-(4-hydroxy-phenyl)-1,1-dimethyl-ethylamino]-ethyl}-4H-benzo[1,4]oxazin-3-one
6-hydroxy-8-{1-hydroxy-2-[2-(4-isopropyl-phenyl)-1.1-dimethyl-ethylamino]-ethyl}-4H-benzo[1,4]oxazin-3-one
8-{2-[2-(4-ethyl-phenyl)-1,1-dimethyl-ethylamino]-1-hydroxy-ethyl}-6-hydroxy-4H-benzo[1,4]oxazin-3-one
8-{2-[2-(4-ethoxy-phenyl)-1,1-dimethyl-ethylamino]-1-hydroxy-ethyl}-6-hydroxy-4H-benzo[1,4]oxazin-3-one
4-(4-{2-[2-hydroxy-2-(6-hydroxy-3-oxo-3,4-dihydro-2H-benzo[1,4]oxazin-8-yl)-ethylamino]-2-methyl-propyl}-phenoxy)-butyric acid
8-{2-[2-(3,4-difluoro-phenyl)-1,1-dimethyl-ethylamino]-1-hydroxy-ethyl}-6-hydroxy-4H-benzo[1,4]oxazin-3-one
1-(4-ethoxy-carbonylamino-3-cyano-5-fluorophenyl)-2-(tert-butylamino)ethanol
2-hydroxy-5-(1-hydroxy-2-{2-[4-(2-hydroxy-2-phenyl-ethylamino)-phenyl]-ethylamino}-ethyl)-benzaldehyde
N-[2-hydroxy-5-(1-hydroxy-2-{2-[4-(2-hydroxy-2-phenyl-ethylamino)-phenyl]-ethylamino}-ethyl)-phenyl]-formamide
8-hydroxy-5-(1-hydroxy-2-{2-[4-(6-methoxy-biphenyl-3-ylamino)-phenyl]-ethylamino}-ethyl)-1H-quinolin-2-one
8-hydroxy-5-[1-hydroxy-2-(6-phenethylamino-hexylamino)-ethyl]-1H-quinolin-2-one
5-[2-(2-{4-[4-(2-amino-2-methyl-propoxy)-phenylamino]-phenyl}-ethylamino)-1-hydroxy-ethyl]-8-hydroxy-1H-quinolin-2-one
[3-(4-{6-[2-hydroxy-2-(4-hydroxy-3-hydroxymethyl-phenyl)-ethylamino]-hexyloxy}-butyl)-5-methyl-phenyl]-urea
4-(2-{6-[2-(2,6-dichloro-benzyloxy)-ethoxy]-hexylamino}-1-hydroxy-ethyl)-2-hydroxymethyl-phenol
[3-(4-{6-[2-hydroxy-2-(4-hydroxy-3-hydroxymethyl-phenyl)-ethylamino]-hexyloxy}-butyl)-benzyl sulphonamide
3-(3-{7-[2-hydroxy-2-(4-hydroxy-3-hydroxymethyl-phenyl)-ethylamino]-heptyloxy}-propyl)-benzylsulphonamide
4-(2-{6-[4-(3-cyclopentanesulphonyl-phenyl)-butoxy]-hexylamino}-1-hydroxy-ethyl)-2-hydroxymethyl-phenol
N-adamantan-2-yl-2-(3-{2-[2-hydroxy-2-(4-hydroxy-3-hydroxymethyl-phenyl)-ethylamino]-propyl}-phenyl)-acetamide, Optionally, in the form of the racemates, enantiomers, diastereomers thereof, and optionally, in the form of the pharmacologically acceptable acid addition salts, solvates or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The anticholinergics used are preferably compounds selected from among the tiotropium salts, preferably the bromide salt, oxitropium salts, preferably the bromide salt, flutropium salts, preferably the bromide salt, ipratropium salts, preferably the bromide salt, glycopyrronium salts, preferably the bromide salt, trospium salts, preferably the chloride salt, tolterodine. In the above-mentioned salts the cations are the pharmacologically active constituents. As anions the above-mentioned salts may preferably contain the chloride, bromide, iodide, sulphate, phosphate, methanesulphonate, nitrate, maleate, acetate, citrate, fumarate, tartrate, oxalate, succinate, benzoate or p-toluenesulphonate, while chloride, bromide, iodide, sulphate, methanesulphonate or p-toluenesulphonate are preferred as counter-ions. Of all the salts the chlorides, bromides, iodides and methanesulphonates are particularly preferred.

Other preferred anticholinergics are selected from among the salts of formula AC-1

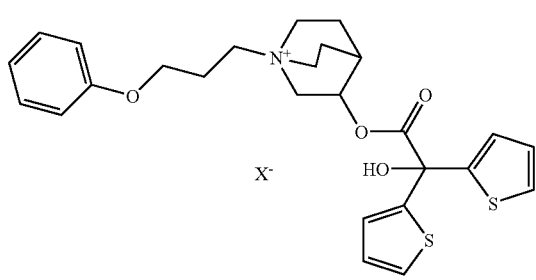

AC-1 wherein X– denotes an anion with a single negative charge, preferably an anion selected from among the fluoride, chloride, bromide, iodide, sulphate, phosphate, methanesulphonate, nitrate, maleate, acetate, citrate, fumarate, tartrate, oxalate, succinate, benzoate and p-toluenesulphonate, preferably an anion with a single negative charge, particularly preferably an anion selected from among the fluoride, chloride, bromide, methanesulphonate and p-toluenesulphonate, particularly preferably bromide, optionally in the form of the racemates, enantiomers or hydrates thereof. Of particular importance are those pharmaceutical combinations which contain the enantiomers of formula AC-1-ene

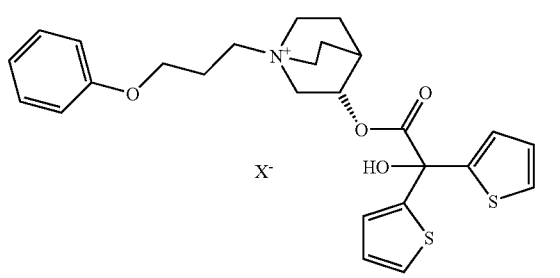

AC-1-ene wherein X– may have the above-mentioned meanings. Other preferred anticholinergics are selected from the salts of formula AC-2

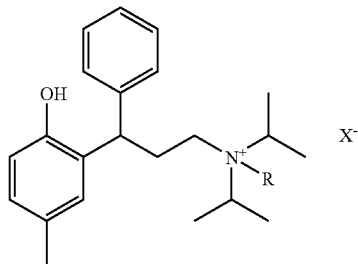

AC-2 wherein R denotes either methyl or ethyl and wherein X– may have the above-mentioned meanings. In an alternativen embodiment the compound of formula AC-2 may also be present in the form of the free base AC-2-base.

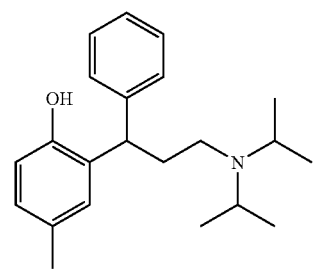

AC-2-base

Other specified compounds are:
tropenol 2,2-diphenylpropionate methobromide,
scopine 2,2-diphenylpropionate methobromide,
scopine 2-fluoro-2,2-diphenylacetate methobromide,
tropenol 2-fluoro-2,2-diphenylacetate methobromide;
tropenol 3,3',4,4'-tetrafluorobenzilate methobromide,
scopine 3,3',4,4'-tetrafluorobenzilate methobromide,
tropenol 4,4'-difluorobenzilate methobromide,
scopine 4,4'-difluorobenzilate methobromide,
tropenol 3,3'-difluorobenzilate methobromide,
scopine 3,3'-difluorobenzilate methobromide;
tropenol 9-hydroxy-fluorene-9-carboxylate methobromide;
tropenol 9-fluoro-fluorene-9-carboxylate methobromide;
scopine 9-hydroxy-fluorene-9-carboxylate methobromide;
scopine 9-fluoro-fluorene-9-carboxylate methobromide;
tropenol 9-methyl-fluorene-9-carboxylate methobromide;
scopine 9-methyl-fluorene-9-carboxylate methobromide;
cyclopropyltropine benzilate methobromide;
cyclopropyltropine 2,2-diphenylpropionate methobromide;
cyclopropyltropine 9-hydroxy-xanthene-9-carboxylate methobromide;
cyclopropyltropine 9-methyl-fluorene-9-carboxylate methobromide;
cyclopropyltropine 9-methyl-xanthene-9-carboxylate methobromide;
cyclopropyltropine 9-hydroxy-fluorene-9-carboxylate methobromide;
cyclopropyltropine methyl 4,4'-difluorobenzilate methobromide.
tropenol 9-hydroxy-xanthene-9-carboxylate methobromide;
scopine 9-hydroxy-xanthene-9-carboxylate methobromide;
tropenol 9-methyl-xanthene-9-carboxylate-methobromide;
scopine 9-methyl-xanthene-9-carboxylate-methobromide;
tropenol 9-ethyl-xanthene-9-carboxylate methobromide;

tropenol 9-difluoromethyl-xanthene-9-carboxylate methobromide;

scopine 9-hydroxymethyl-xanthene-9-carboxylate methobromide,

The above-mentioned compounds may also be used as salts within the scope of the present invention, wherein instead of the methobromide the salts metho-X are used, wherein X may have the meanings given hereinbefore for X–. As corticosteroids it is preferable to use compounds selected from among beclomethasone, betamethasone, budesonide, butixocort, ciclesonide, deflazacort, dexamethasone, etiprednol, flunisolide, fluticasone, loteprednol, mometasone, prednisolone, prednisone, rofleponide, triamcinolone, RPR-106541, NS-126, ST-26 and (S)-fluoromethyl 6,9-difluoro-17-[(2-furanylcarbonyl)oxy]-11-hydroxy-16-methyl-3-oxo-androsta-1,4-diene-17-carbothionate (S)-(2-oxo-tetrahydro-furan-3 S-yl)6,9-difluoro-11-hydroxy-16-methyl-3-oxo-17-propionyloxy-androsta-1,4-diene-17-carbothionate, cyanomethyl 6α,9α-difluoro-11β-hydroxy-16α-methyl-3-oxo-17α-(2,2,3,3-tetramethylcyclopropylcarbonyl)oxy-androsta-1,4-diene-17β-carboxylate optionally, in the form of the racemates, enantiomers or diastereomers thereof and optionally in the form of the salts and derivatives thereof, the solvates and/or hydrates thereof. Any reference to steroids includes a reference to any salts or derivatives, hydrates or solvates thereof which may exist. Examples of possible salts and derivatives of the steroids may be: alkali metal salts, such as for example sodium or potassium salts, sulphobenzoates, phosphates, isonicotinates, acetates, dichloroacetates, propionates, dihydrogen phosphates, palmitates, pivalates or furoates.

PDE4-inhibitors which may be used are preferably compounds selected from among enprofyllin, theophyllin, roflumilast, ariflo (cilomilast), tofimilast, pumafentrin, lirimilast, arofyllin, atizoram, D-4418, Bay-198004, BY343, CP-325, 366, D-4396 (Sch-351591), AWD-12-281 (GW-842470), NCS-613, CDP-840, D-4418, PD-168787, T-440, T-2585, V-11294A, Cl-1018, CDC-801, CDC-3052, D-22888, YM-58997, Z-15370 and N-(3,5-dichloro-1-oxo-pyridin-4-yl)-4-difluoromethoxy-3-cyclopropylmethoxybenzamide (–)p-[(4aR*,10bS*)-9-ethoxy-1,2,3,4,4a,10b-hexahydro-8-methoxy-2-methylbenzo[s][1,6]naphthyridin-6-yl]-N,N-diisopropylbenzamide (R)-(+)-1-(4-bromobenzyl)-4-[(3-cyclopentyloxy)-4-methoxyphenyl]-2-pyrrolidone 3-(cyclopentyloxy-4-methoxyphenyl)-1-(4-N'-[N-2-cyano-S-methyl-isothioureido]benzyl)-2-pyrrolidone cis[4-cyano-4-(3-cyclopentyloxy-4-methoxyphenyl)cyclohexane-1-carboxylic acid]

2-carbomethoxy-4-cyano-4-(3-cyclopropylmethoxy-4-difluoromethoxy-phenyl)cyclohexan-1-one cis[4-cyano-4-(3-cyclopropylmethoxy-4-difluoromethoxyphenyl)cyclohexan-1-ol]

(R)-(+)-ethyl[4-(3-cyclopentyloxy-4-methoxyphenyl)pyrrolidin-2-ylidene]acetate (S)-(–)-ethyl[4-(3-cyclopentyloxy-4-methoxyphenyl)pyrrolidin-2-ylidene]acetate 9-cyclopentyl-5,6-dihydro-7-ethyl-3-(2-thienyl)-9H-pyrazolo[3,4-c]-1,2,4-triazolo[4,3-a]pyridine 9-cyclopentyl-5,6-dihydro-7-ethyl-3-(tert-butyl)-9H-pyrazolo[3,4-c]-1,2,4-triazolo[4,3-a]pyridine optionally in the form of the racemates, enantiomers or diastereomers thereof and optionally in the form of the pharmacologically acceptable acid addition salts thereof, the solvates and/or hydrates thereof. According to the invention the acid addition salts of the PDE4 inhibitors are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The LTD4-antagonists used are preferably compounds selected from among montelukast, pranlukast, zafirlukast, MCC-847 (ZD-3523), MN-001, MEN-91507 (LM-1507), VUF-5078, VUF-K-8707, L-733321 and 1-(((R)-(3-(2-(6,7-difluoro-2-quinolinyl)ethenyl)phenyl)-3-(2-(2-hydroxy-2-propyl)phenyl)thio)methylcyclopropane-acetic acid, 1-(((1(R)-3(3-(2-(2,3-dichlorothieno[3,2-b]pyridin-5-yl)-(E)-ethenyl)phenyl)-3-(2-(1-hydroxy-1-methylethyl)phenyl)propyl)thio)methyl)cyclopropaneacetic acid

[2-[[2-(4-tert-butyl-2-thiazolyl)-5-benzofuranyl]oxymethyl]phenyl]acetic acid

Optionally, in the form of the racemates, enantiomers or diastereomers thereof and optionally in the form of the pharmacologically acceptable acid addition salts, solvates and/or hydrates thereof. According to the invention these acid addition salts are preferably selected from among the hydrochloride, hydrobromide, hydroiodide, hydrosulphate, hydrophosphate, ydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate. By salts or derivatives which the LTD4-antagonists may optionally be capable of forming are meant, for example: alkali metal salts, such as for example sodium or potassium salts, alkaline earth metal salts, sulphobenzoates, phosphates, isonicotinates, acetates, propionates, dihydrogen phosphates, palmitates, pivalates or furoates.

EGFR-inhibitors which may be used are preferably compounds selected from among cetuximab, trastuzumab, ABX-EGF, Mab ICR-62 and 4-[(3-chloro-4-fluorophenyl)amino]-6-{[4-(morpholin-4-yl)-1-oxo-2-buten-1-yl]-amino}-7-cyclopropylmethoxy-quinazoline 4-[(3-chloro-4-fluorophenyl)amino]-6-{[4-(N,N-di ethylamino)-1-oxo-2-buten-1-yl]-amino}-7-cyclopropyl-methoxy-quinazoline 4-[(3-chloro-4-fluorophenyl)amino]-6-{[4-(N,N-dimethylamino)-1-oxo-2-buten-1-yl]amino}-7-cyclopropyl-methoxy-quinazoline 4-[(R)-(1-phenyl-ethyl)amino]-6-{[4-(morpholin-4-yl)-1-oxo-2-buten-1-yl]amino}-7-cyclopentyloxy-quinazoline 4-[(3-chloro-4-fluoro-phenyl)amino]-6-{[4-((R)-6-methyl-2-oxo-morpholin-4-yl)-1-oxo-2-buten-1-yl]amino}-7-cyclopropylmethoxy-quinazoline 4-[(3-chloro-4-fluoro-phenyl)amino]-6-{[4-((R)-6-methyl-2-oxo-morpholin-4-yl)-1-oxo-2-buten-1-yl]amino}-7-[(S)-(tetrahydrofuran-3-yl)oxy]-quinazoline 4-[(3-chloro-4-fluoro-phenyl)amino]-6-{[4-((R)-2-methoxymethyl-6-oxo-morpholin-4-yl)-1-oxo-2-buten-1-yl]amino}-7-cyclopropylmethoxy-quinazoline 4-[(3-chloro-4-fluoro-phenyl)amino]-6-[2-((S)-6-methyl-2-oxo-morpholin-4-yl)-ethoxy]-7-methoxy-quinazoline 4-[(3-chloro-4-fluorophenyl)amino]-6-({4-[N-(2-methoxyethyl)-N-methyl-amino]-1-oxo-2-buten-1-yl}amino)-7-cyclopropylmethoxy-quinazoline 4-[3-chloro-4-fluorophenyl)amino]-6-{[4-(N,N-dimethylamino)-1-oxo-2-buten-1-yl]amino}-7-cyclopentyloxy-quinazoline 4-[(R)-(1-phenyl-ethyl)amino]-6-{[4-(N,N-bis-(2-methoxy-ethyl)-amino)-1-oxo-2-buten-1-yl]amino}-7-cyclopropylmethoxy-quinazoline
4-[(R)-(1-phenyl-ethyl)amino]-6-({4-[N-(2-methoxy-ethyl)-N-ethyl-amino]-1-oxo-2-buten-1-yl}amino)-7-cyclopropylmethoxy-quinazoline
4-[(R)-(1-phenyl-ethyl)amino]-6-({4-[N-(2-methoxy-ethyl)-N-methyl-amino]-1-oxo-2-buten-1-yl}amino)-7-cyclopropylmethoxy-quinazoline
4-[(R)-(1-phenyl-ethyl)amino]-6-({4-[N-(tetrahydropyran-4-yl)-N-methyl-amino]-1-oxo-2-buten-1-yl}amino)-7-cyclopropylmethoxy-quinazoline
4-[(3-chloro-4-fluorophenyl)amino]-6-{[4-(N,N-dimethylamino)-1-oxo-2-buten-1-yl]amino}-7-((R)-tetrahydrofuran-3-yloxy)-quinazoline
4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline
4-[(3-chloro-4-fluorophenyl)amino]-6-({4-[N-(2-methoxy-ethyl)-N-methyl-amino]-1-oxo-2-buten-1-yl}amino)-7-cyclopentyloxy-quinazoline
4-[(3-chloro-4-fluorophenyl)amino]-6-{[4-(N-cyclopropyl-N-methyl-amino)-1-oxo-2-buten-1-yl]amino}-7-cyclopentyloxy-quinazoline
4-[(3-chloro-4-fluorophenyl)amino]-6-{[4-(N,N-dimethylamino)-1-oxo-2-buten-1-yl]amino}-7-[(R)-(tetrahydrofuran-2-yl)methoxy]-quinazoline
4-[(3-chloro-4-fluorophenyl)amino]-6-{[4-(N,N-dimethylamino)-1-oxo-2-buten-1-yl]amino}-7-[(S)-(tetrahydrofuran-2-yl)methoxy]-quinazoline
4-[(3-ethynyl-phenyl)amino]-6.7-bis-(2-methoxy-ethoxy)-quinazoline
4-[(3-chloro-4-fluorophenyl)amino]-7-[3-(morpholin-4-yl)-propyloxy]-6-[(vinyl-carbonyl)amino]-quinazoline
4-[(R)-(1-phenyl-ethyl)amino]-6-(4-hydroxy-phenyl)-7H-pyrrolo[2,3-d]pyrimidine
3-cyano-4-[(3-chloro-4-fluorophenyl)amino]-6-{[4-(N,N-dimethylamino)-1-oxo-2-buten-1-yl]amino}-7-ethoxy-quinoline
4-{[3-chloro-4-(3-fluoro-benzyloxy)-phenyl]amino}-6-(5-{[(2-methanesulphonyl-ethyl)amino]methyl}-furan-2-yl)quinazoline
4-[(R)-(1-phenyl-ethyl)amino]-6-{[4-((R)-6-methyl-2-oxo-morpholin-4-yl)-1-oxo-2-buten-1-yl]amino}-7-methoxy-quinazoline
4-[(3-chloro-4-fluorophenyl)amino]-6-{[4-(morpholin-4-yl)-1-oxo-2-buten-1-yl]-amino}-7-[(tetrahydrofuran-2-yl)methoxy]-quinazoline
4-[(3-chloro-4-fluorophenyl)amino]-6-({4-[N,N-bis-(2-methoxy-ethyl)-amino]-1-oxo-2-buten-1-yl}amino)-7-[(tetrahydrofuran-2-yl)methoxy]-quinazoline
4-[(3-ethynyl-phenyl)amino]-6-{[4-(5.5-dimethyl-2-oxo-morpholin-4-yl)-1-oxo-2-buten-1-yl]amino}-quinazoline
4-[(3-chloro-4-fluoro-phenyl)amino]-6-[2-(2.2-dimethyl-6-oxo-morpholin-4-yl)-ethoxy]-7-methoxy-quinazoline
4-[(3-chloro-4-fluoro-phenyl)amino]-6-[2-(2.2-dimethyl-6-oxo-morpholin-4-yl)-ethoxy]-7-[(R)-(tetrahydrofuran-2-yl)methoxy]-quinazoline
4-[(3-chloro-4-fluoro-phenyl)amino]-7-[2-(2.2-dimethyl-6-oxo-morpholin-4-yl)-ethoxy]-6-[(S)-(tetrahydrofuran-2-yl)methoxy]-quinazoline
4-[(3-chloro-4-fluoro-phenyl)amino]-6-{2-[4-(2-oxo-morpholin-4-yl)-piperidin-1-yl]-ethoxy}-7-methoxy-quinazoline
4-[(3-chloro-4-fluoro-phenyl)amino]-6-[1-(tert.-butyloxycarbonyl)-piperidin-4-yloxy]-7-methoxy-quinazoline
4-[(3-chloro-4-fluoro-phenyl)amino]-6-(trans-4-amino-cyclohexan-1-yloxy)-7-methoxy-quinazoline
4-[(3-chloro-4-fluoro-phenyl)amino]-6-(trans-4-methanesulphonylamino-cyclohexan-1-yloxy)-7-methoxy-quinazoline
4-[(3-chloro-4-fluoro-phenyl)amino]-6-(tetrahydropyran-3-yloxy)-7-methoxy-quinazoline
4-[(3-chloro-4-fluoro-phenyl)amino]-6-(1-methyl-piperidin-4-yloxy)-7-methoxy-quinazoline
4-[(3-chloro-4-fluoro-phenyl)amino]-6-{1-[(morpholin-4-3/1)carbonyl]-piperidin-4-yloxy}-7-methoxy-quinazoline
4-[(3-chloro-4-fluoro-phenyl)amino]-6-{1-[(methoxymethyl)carbonyl]-piperidin-4-yloxy}-7-methoxy-quinazoline
4-[(3-chloro-4-fluoro-phenyl)amino]-6-(piperidin-3-yloxy)-7-methoxy-quinazoline
4-[(3-chloro-4-fluoro-phenyl)amino]-6-[1-(2-acetylamino-ethyl)-piperidin-4-yloxy]-7-methoxy-quinazoline
4-[(3-chloro-4-fluoro-phenyl)amino]-6-(tetrahydropyran-4-yloxy)-7-ethoxy-quinazoline
4-[(3-chloro-4-fluoro-phenyl)amino]-6-((S)-tetrahydrofuran-3-yloxy)-7-hydroxy-quinazoline
4-[(3-chloro-4-fluoro-phenyl)amino]-6-(tetrahydropyran-4-yloxy)-7-(2-methoxy-ethoxy)-quinazoline
4-[(3-chloro-4-fluoro-phenyl)amino]-6-{trans-4-[(dimethylamino)sulphonylamino]-cyclohexan-1-yloxy}-7-methoxy-quinazoline
4-[(3-chloro-4-fluoro-phenyl)amino]-6-{trans-4-[(morpholin-4-yl)carbonylamino]-cyclohexan-1-yloxy}-7-methoxy-quinazoline
4-[(3-chloro-4-fluoro-phenyl)amino]-6-{trans-4-[(morpholin-4-yl)sulphonylamino]-cyclohexan-1-yloxy}-7-methoxy-quinazoline
4-[(3-chloro-4-fluoro-phenyl)amino]-6-(tetrahydropyran-4-yloxy)-7-(2-acetylamino-ethoxy)-quinazoline
4-[(3-chloro-4-fluoro-phenyl)amino]-6-(tetrahydropyran-4-yloxy)-7-(2-methanesulphonylamino-ethoxy)-quinazoline
4-[(3-chloro-4-fluoro-phenyl)amino]-6-{1-[(piperidin-1-yl)carbonyl]-piperidin-4-yloxy}-7-methoxy-quinazoline
4-[(3-chloro-4-fluoro-phenyl)amino]-6-(1-aminocarbonylmethyl-piperidin-4-yloxy)-7-methoxy-quinazoline
4-[(3-chloro-4-fluoro-phenyl)amino]-6-(cis-4-{N-[(tetrahydropyran-4-yl)carbonyl]-N-methyl-amino}-cyclohexan-1-yloxy)-7-methoxy-quinazoline
4-[(3-chloro-4-fluoro-phenyl)amino]-6-(cis-4-{N-[(morpholin-4-yl)carbonyl]-N-methyl-amino}-cyclohexan-1-yloxy)-7-methoxy-quinazoline
4-[(3-chloro-4-fluoro-phenyl)amino]-6-(cis-4-{N-[(morpholin-4-yl)sulphonyl]-N-methyl-amino}-cyclohexan-1-yloxy)-7-methoxy-quinazoline
4-[(3-chloro-4-fluoro-phenyl)amino]-6-(trans-4-ethansulphonylamino-cyclohexan-1-yloxy)-7-methoxy-quinazoline
4-[(3-chloro-4-fluoro-phenyl)amino]-6-(1-methanesulphonyl-piperidin-4-yloxy)-7-ethoxy-quinazoline
4-[(3-chloro-4-fluoro-phenyl)amino]-6-(1-methanesulphonyl-piperidin-4-yloxy)-7-(2-methoxy-ethoxy)-quinazoline
4-[(3-chloro-4-fluoro-phenyl)amino]-6-[1-(2-methoxy-acetyl)-piperidin-4-yloxy]-7-(2-methoxy-ethoxy)-quinazoline
4-[(3-chloro-4-fluoro-phenyl)amino]-6-(cis-4-acetylamino-cyclohexan-1-yloxy)-7-methoxy-quinazoline
4-[(3-ethynyl-phenyl)amino]-6-[1-(tert.-butyloxycarbonyl)-piperidin-4-yloxy]-7-methoxy-quinazoline 4-[(3-ethynyl-phenyl)amino]-6-(tetrahydropyran-4-yloxy]-7-methoxy-quinazoline
4-[(3-chloro-4-fluoro-phenyl)amino]-6-(cis-4-{N-[(piperidin-1-yl)carbonyl]-N-methyl-amino}-cyclohexan-1-yloxy)-7-methoxy-quinazoline
4-[(3-chloro-4-fluoro-phenyl)amino]-6-(cis-4-{N-[(4-methyl-piperazin-1-yl)carbonyl]-N-methyl-amino}-cyclohexan-1-yloxy)-7-methoxy-quinazoline
4-[(3-chloro-4-fluoro-phenyl)amino]-6-{cis-4-[(morpholin-4-yl)carbonylamino]-cyclohexan-1-yloxy}-7-methoxy-quinazoline
4-[(3-chloro-4-fluoro-phenyl)amino]-6-{1-[2-(2-oxopyrrolidin-1-yl)ethyl]-piperidin-4-yloxy}-7-methoxy-quinazoline
4-[(3-chloro-4-fluoro-phenyl)amino]-6-{1-[(morpholin-4-yl)carbonyl]-piperidin-4-yloxy}-7-(2-methoxy-ethoxy)-quinazoline
4-[(3-ethynyl-phenyl)amino]-6-(1-acetyl-piperidin-4-yloxy)-7-methoxy-quinazoline
4-[(3-ethynyl-phenyl)amino]-6-(1-methyl-piperidin-4-yloxy)-7-methoxy-quinazoline
4-[(3-ethynyl-phenyl)amino]-6-(1-methanesulphonyl-piperidin-4-yloxy)-7-methoxy-quinazoline
4-[(3-chloro-4-fluoro-phenyl)amino]-6-(1-methyl-piperidin-4-yloxy)-7(2-methoxy-ethoxy)-quinazoline
4-[(3-chloro-4-fluoro-phenyl)amino]-6-(1-isopropyloxycarbonyl-piperidin-4-yloxy)-7-methoxy-quinazoline
4-[(3-chloro-4-fluoro-phenyl)amino]-6-(cis-4-methylamino-cyclohexan-1-yloxy)-7-methoxy-quinazoline
4-[(3-chloro-4-fluoro-phenyl)amino]-6-{cis-4-[N-(2-methoxy-acetyl)-N-methyl-amino]-cyclohexan-1-yloxy}-7-methoxy-quinazoline
4-[(3-ethynyl-phenyl)amino]-6-(piperidin-4-yloxy)-7-methoxy-quinazoline
4-[(3-ethynyl-phenyl)amino]-6-{1-(2-methoxy-acetyl)-piperidin-4-yloxy}-7-methoxy-quinazoline
4-[(3-ethynyl-phenyl)amino]-6-{1-[(morpholin-4-yl)carbonyl]-piperidin-4-yloxy}-7-methoxy-quinazoline
4-[(3-chloro-4-fluoro-phenyl)amino]-6-{1-[(cis-2,6-dimethyl-morpholin-4-yl)carbonyl]-piperidin-4-yloxy}-7-methoxy-quinazoline
4-[(3-chloro-4-fluoro-phenyl)amino]-6-{1-[(2-methyl-morpholin-4-yl)carbonyl]-piperidin-4-yloxy}-7-methoxy-quinazoline
4-[(3-chloro-4-fluoro-phenyl)amino]-6-{1-[(S,S)-(2-oxa-5-aza-bicyclo[2,2,1]hept-5-yl)carbonyl]-piperidin-4-yloxy}-7-methoxy-quinazoline
4-[(3-chloro-4-fluoro-phenyl)amino]-6-{1-[(N-methyl-N-2-methoxyethyl-amino)carbonyl]-piperidin-4-yloxy}-7-methoxy-quinazoline
4-[(3-chloro-4-fluoro-phenyl)amino]-6-(1-ethyl-piperidin-4-yloxy)-7-methoxy-quinazoline
4-[(3-chloro-4-fluoro-phenyl)amino]-6-{1-[(2-methoxyethyl)carbonyl]-piperidin-4-yloxy}-7-methoxy-quinazoline
4-[(3-chloro-4-fluoro-phenyl)amino]-6-{1-[(3-methoxypropyl-amino)-carbonyl]-piperidin-4-yloxy}-7-methoxy-quinazoline
4-[(3-chloro-4-fluoro-phenyl)amino]-6-[cis-4-(N-methanesulphonyl-N-methyl-amino)-cyclohexan-1-yloxy]-7-methoxy-quinazoline
4-[(3-chloro-4-fluoro-phenyl)amino]-6-[cis-4-(N-acetyl-N-methyl-amino)-cyclohexan-1-yloxy]-7-methoxy-quinazoline
4-[(3-chloro-4-fluoro-phenyl)amino]-6-(trans-4-methylamino-cyclohexan-1-yloxy)-7-methoxy-quinazoline
4-[(3-chloro-4-fluoro-phenyl)amino]-6-[trans-4-(N-methanesulphonyl-N-methyl-amino)-cyclohexan-1-yloxy]-7-methoxy-quinazoline
4-[(3-chloro-4-fluoro-phenyl)amino]-6-(trans-4-dimethylamino-cyclohexan-1-yloxy)-7-methoxy-quinazoline
4-[(3-chloro-4-fluoro-phenyl)amino]-6-(trans-4-{N-[(morpholin-4-yl)carbonyl]-N-methyl-amino}-cyclohexan-1-yloxy)-7-methoxy-quinazoline
4-[(3-chloro-4-fluoro-phenyl)amino]-6-[2-(2.2-dimethyl-6-oxo-morpholin-4-yl)-ethoxy]-7-[(S)-(tetrahydrofuran-2-yl)methoxy]-quinazoline
4-[(3-chloro-4-fluoro-phenyl)amino]-6-(1-methanesulphonyl-piperidin-4-yloxy)-7-methoxy-quinazoline
4-[(3-chloro-4-fluoro-phenyl)amino]-6-(1-cyano-piperidin-4-yloxy)-7-methoxy-quinazoline Optionally, in the form of the racemates, enantiomers, diastereomers thereof, and optionally, in the form of the pharmacologically acceptable acid addition salts, solvates or hydrates thereof. According to the invention these acid addition salts are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The dopamine agonists used are preferably compounds selected from among bromocriptin, cabergoline, alpha-dihydroergocryptine, lisuride, pergolide, pramipexol, roxindol, ropinirol, talipexol, tergurid and viozan, optionally in the form of the racemates, enantiomers, diastereomers thereof and optionally in the form of the pharmacologically acceptable acid addition salts, solvates or hydrates thereof. According to the invention these acid addition salts are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydrooxalate, hydro succinate, hydrobenzoate and hydro-p-toluenesulphonate.

H1-Antihistamines which may be used are preferably compounds selected from among epinastine, cetirizine, azelastine, fexofenadine, levocabastine, loratadine, mizolastine, ketotifen, emedastine, dimetindene, clemastine, bamipine, cexchlorpheniramine, pheniramine, doxylamine, chlorphenoxamine, dimenhydrinate, diphenhydramine, promethazine, ebastine, desloratidine and meclozine, optionally in the form of the racemates, enantiomers, diastereomers thereof and optionally in the form of the pharmacologically acceptable acid addition salts, solvates or hydrates thereof. According to the invention these acid addition salts are preferably selected from among the hydrochloride, hydrobromide, hydriodide, hydrosulphate, hydrophosphate, hydromethanesulphonate, hydronitrate, hydro maleate, hydroacetate, hydrocitrate, hydrofumarate, hydrotartrate, hydroxalate, hydrosuccinate, hydrobenzoate and hydro-p-toluenesulphonate.

Besides inhalable macromolecules may be used, as disclosed in European Patent Application EP 1 003 478.

In addition, the compound may from the group of the derivatives of ergot alkaloids, triptanes, CGRP-inhibitors, phosphodiesterase-V inhibitors, optionally in the form of the racemates, enantiomers or diastereomers thereof, optionally in the form of the pharmacologically acceptable acid addition salts, solvates and/or hydrates thereof.

Examples of ergot alkaloid derivatives are: dihydroergotamine, ergotamine.

Examples of substances suitable for inhalation include medicaments, medicament formulations and mixtures containing the above-mentioned active substances, and the salts and esters thereof and combinations of these active substances, salts and esters.

In the following the invention is described in connection with simplified schematic figures and examples.

BRIEF DESCRIPTION OF THE DRAWINGS

FIG. 2 represents a medicine dispensation device,

FIG. 3 represents a further medicine dispensation device, and

DETAILED DESCRIPTION OF THE INVENTION

Figure 1:
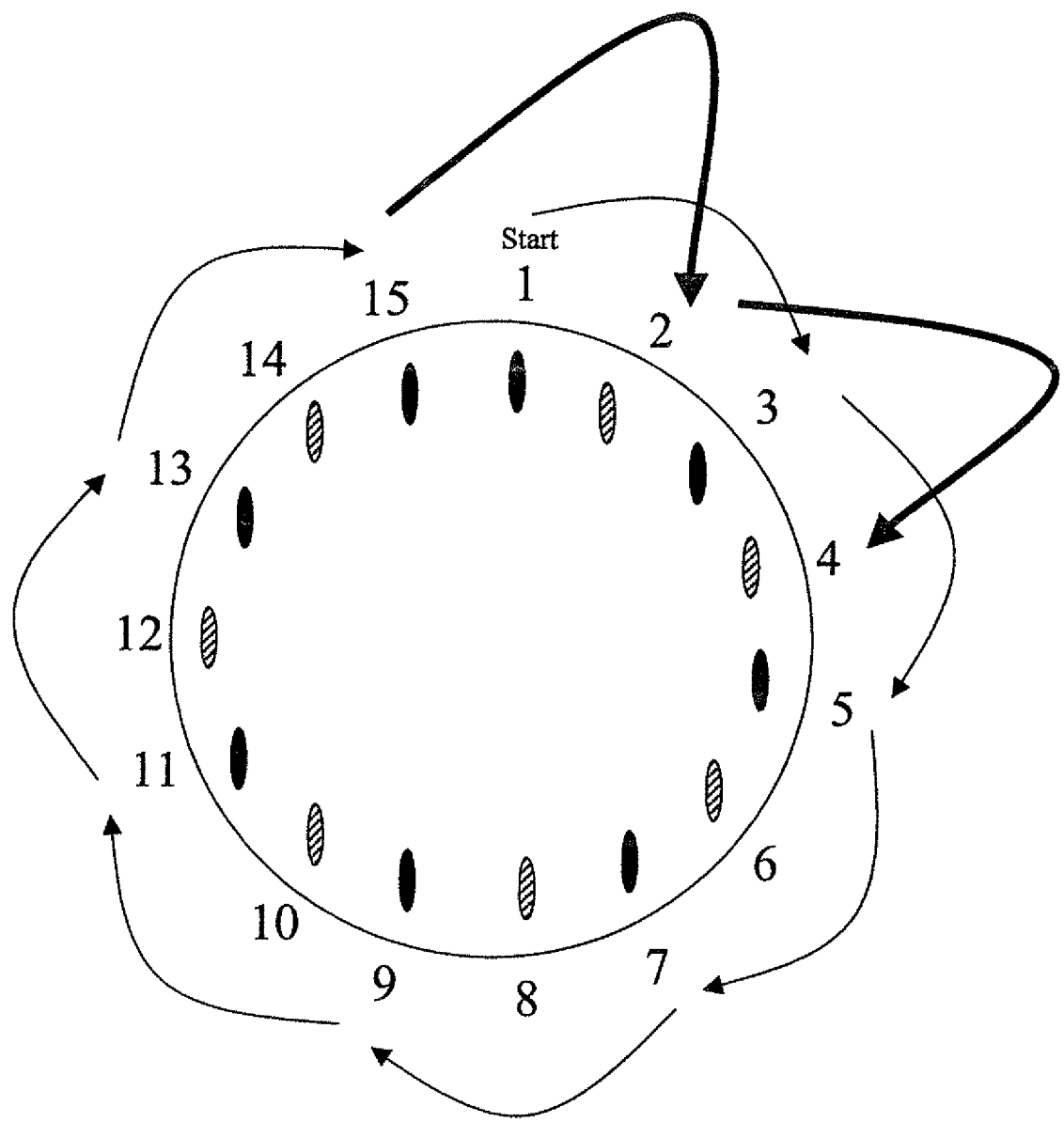
FIG. 1 shows a medicine magazine with two groups of medicine chambers.

FIG. 1 illustrates the principle of the medicine dispensation device according to the invention with the medicine chambers placed in a circular and equidistant alignment. The total of 15 medicine chambers is divided into two groups with all of the medicine chambers being positioned centered along a single endless path. The first group of medicine chambers is represented by black oviform and the second group by semi-shaded oviform. Starting with a first medicine chamber no. 1, when this is used up the chamber next-but-one, i.e. no. 3, is targetted, then no. 5, etc., until every chamber of group 1 has been arrived at and used up. The position of the last chamber of group 1, in this case no. 15, is adjacent to chamber no. 1, thus at half the advancing distance. Maintaining the applied advancing distance, e.g. by advancing the mouthpiece or the magazine or the container, the first chamber of the second group, no. 2, is reached. Then every chamber of group 2 is approached in succession, each time skipping a used-up chamber of group 1.

A drug indicator, showing which chamber is in use or how many full chambers are still in the magazine, preferably numbers the chambers in order of use.

In this example, alternate chambers are targeted. After nearly a full turn, equivalent to one full rotation minus half an advancing distance, the target switches from a first group of medicine chambers to a second group.

From this example it is obvious that, depending on advancing distance and alignment density of the medicine magazines, a skipping of two, three, or more medicine chambers may be required or advantageous. Accordingly, the chambers are divided into three, four, or more groups, wherein the distance between the last chamber of the first group and the first chamber of the first group is preferably shorter than the advancing distance.

This example further shows an equidistant arrangement of all medicine chambers (although not of the individual groups) and an equidistant advance adjusted accordingly. Such an embodiment is advantageous for a medicine magazine due to its simple geometry and for the advance due to its continuous motion and therefore simple mechanism.

FIG. 2 shows a disc-like inhalation device, e.g., a multiple-dose powder inhalator with a mouthpiece 2 attached to its outer circumference. The digits 1 to 9 indicate the medicine-chamber and intake positions in the order in which they are approached. Excepting no. 9, the intermediate chamber positions are not illustrated. In this embodiment, the mouthpiece 2 is aligned with the next medicine chamber by a predetermined advance 3, indicated here by arrows. The darker advancing arrow extending radially corresponds essentially with the advancing direction of the mouthpiece, while the broken curved arrow corresponds with the advancing distance of a mouthpiece or of an internal mechanism, which must comprise a certain elevation prior to the alignment with a new medicine chamber, e.g., for the purpose of piercing.

There is no equidistant advance between the positions 8 and 9. Such an additional advance between one group and the next can be performed by a relevant mechanism in the casing 1 and simultaneously used as indicator. Such an indicator may e.g., serve as an additional reference between individual medication dosages or compositions, e.g., week 1/week 2, month 1: low dosage/month 2: higher dosage, or day 1 to 10: first drug/day 11 to 16: second drug.

The different positions of the mouthpiece 2 in the medicine chamber positions 2 to 9 are indicated in the figure by broken lines.

FIG. 3 shows a tracked continuous blister-loop 4 inserted in a drug-dispensation device. The blister loop is moved along by the mouthpiece 2, which is mobile but fixed to the casing 1. On one side of the mouthpiece alternate blisters are indicated as used-up medicine chambers 5. The medicine magazine moves in relation to the mouthpiece and the casing, and different mouthpiece positions are indicated by broken line.

What is claimed is:

1. Medicine dispensing device for the dispensing of individual doses of medicine, comprising:

a medicine magazine having a multitude of medicine chambers arranged in a single continuous loop in the medicine magazine, wherein the center points of each medicine chamber is positioned along the single endless path, wherein the medicine chambers are arranged equidistantly in the medicine magazine, a mouthpiece through which individual doses of medicine are dispensed from the medicine chambers, the mouthpiece and magazine being movable relative to each other for aligning each medicine chamber with the mouthpiece, wherein the medicine chambers are arranged in groups, the chambers of each group being arranged on said single endless path defining continuous loop with the chambers of the groups being interspersed with each other along said single endless path in a manner causing, while continuing to follow said single endless path after an essentially complete rotation of the medicine magazine from a position in which the mouthpiece is in an initial medicine chamber position x in alignment with a chamber of a first of said groups and only chambers of said first group are sequentially opened with chambers of at least one other group being skipped over in going from one chamber of the first group to a subsequent chamber of the first group, is in a medicine chamber position in alignment with a chamber of another group of chambers at a medicine chamber position x+1 or x−1 that sequentially follows or precedes said initial medicine chamber position x so that only chambers of the other of the group of chambers are sequentially opened during the next essentially complete rotation of the medicine magazine from the medicine chamber position x+1 or x−1 with at least the chambers of the first group being skipped over in going from one chamber of the other group to a subsequent chamber of the other group.

2. Medicine dispensing device according to claim 1, wherein the mouthpiece and the medicine magazine can only be moved in one direction in relation to each other.

3. Medicine dispensing device according to claim 1, wherein the chambers of one, two or three groups are situated between two consecutive chambers of the same group of medicine chambers.

4. Medicine dispensing device according to claim 1, wherein the medicine magazine is accommodated in an essentially disc-shaped casing and wherein the mouthpiece is situated on and can be shifted along the outer circumference of the disc-shaped casing.

5. Medicine dispensing device according to claim 1, wherein medicine magazine is fixed in relation to the casing while the mouthpiece is in operation.

6. Medicine dispensing device according to claim 1, wherein the medicine chambers are arranged in a circle in the medicine magazine.

7. Medicine dispensing device according to claim 1, wherein the medicine chambers are arranged in a continuous loop blister band (4).

8. Medicine dispensing device according to claim 1, further comprising an indicator to indicate which medicine chamber the mouthpiece is situated in alignment with.

9. Medicine dispensing device according to claim 1, wherein the device is a multiple-dose powder inhalator.

10. Medicine dispensing device according to claim 1, wherein the multitude of medicine chambers is a number of chambers that does not exceed 30 or 60.

11. Medicine dispensing device according to claim 1, for the administering a drug that contains an active substance or a combination of active substances selected from the group of betamimetics, anticholinergics, steroids, antiallergens, derivatives of ergotalkaloids, triptane, CGRP-antagonists, phosphodiesterase-V-inhibitors, phosphodiesterase-IV-inhibitors, LTD4-antagonists, and EGFR-kinase-inhibitor.

* * * * *